United States Patent [19]

Mack et al.

[11] Patent Number: Plant 7,642

[45] Date of Patent: Sep. 3, 1991

[54] CHRYSANTHEMUM PLANT NAMED GRACE

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 526,497

[22] Filed: May 21, 1990

[51] Int. Cl.[5] ..... A01H 5/00

[52] U.S. Cl. ..... Plt./74

[58] Field of Search ..... Plt./74, 74.1, 75, 82.2, Plt./82.3

*Primary Examiner*—Howard J. Locker

*Attorney, Agent, or Firm*—Foley & Lardner

[57] ABSTRACT

A Chrysanthemum plant named Grace particularly characterized by its flat capitulum form; daisy capitulum form; daisy capitulum type; orange-bronze ray floret color with a yellow halo around the corolla of disc florets; diameter across face of capitulum of 44 to 57 mm when fully opened; spreading and prolific branching pattern; average natural season flowering date of August 27 in Salinas, Calif. and September 27 in Hightstown, N.J.; uniform seven week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandiflora*, and referred to by the cultivar name Grace.

Grace, identified as 83-628001, was originated from a controlled selfing made by Grace H. Mack in a controlled breeding program in New Canaan, Conn., in 1982.

The selfed parent of Grace was an unnamed seedling, identified as 81-M33001, a bronze daisy garden mum.

Grace was discovered and selected as one flowering plant within the progeny of the stated cross by Cornelis P. VandenBerg in October 1983, in a controlled environment in Salinas, Calif.

The first act of asexual reproduction of Grace was accomplished when vegetative cuttings were taken from the initial selection in December 1983 in a controlled environment in Salinas, Calif., by technicians working under the supervision of Cornelis P. VandenBerg.

Horticultural examination of controlled flowerings of successive plantings has shown that the unique combination of characteristics as herein disclosed for Grace are firmly fixed and are retained through successive generations of asexual reproduction.

Grace has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Grace, which, in combination, distinguish this Chrysanthemum as a new and distinct cultivar:

1. Flat capitulum form.
2. Daisy capitulum type.

3. Orange-bronze ray floret color, with the base of the florets being yellow to form a yellow halo around the corolla of disc florets.
4. Diameter across face of capitulum of 44 to 57 mm when fully opened.
5. Medium plant height, averaging 28 to 36 cm from soil line at time of flowering, based on June 15 planting under natural daylength at Hightstown, N.J.
6. Spreading and prolific branching pattern, with an average of 7–8 branches per plant after pinch two weeks after planting a rooted cutting in Hightstown, N.J.
7. Average natural season flower date of August 27 in Salinas, Calif., and September 27 in Hightstown, N.J., based on several years of trial flowering.
8. Uniform seven week photoperiodic flowering response to short days in photoperiodic controlled flowering programs.
9. Durable, uniform performance.

The above measurements represent repeated flowerings over a period of a minimum of two years.

The accompanying photographic drawings show typical inflorescence and leaf characteristics of Grace, with the colors being as nearly true as possible with illustrations of this type.

Sheet 1 is a color photograph of Grace grown as a pinched spray pot mum in a 15 cm pot.

Sheet 2 is a black and white photograph of three views of the inflorescence of Grace.

Sheet 3 is a black and white photograph showing the upper and under sides of the leaves of Grace at three stages of development (mature, intermediate and immature).

Of the commercial garden mum cultivars known to the inventors, the most similar in comparison to Grace is the cultivar Wolverine, disclosed in U.S. Plant Pat. No. 4,312. Reference is made to attached Chart A, which compares certain characteristics of Grace to the same characteristics of Wolverine.

Similar traits are capitulum form, plant height and controlled response. Although the ray floret color of both Grace and Wolverine are generally described as orange-bronze, the ray floret color of Grace is a much more bright and lively orange-bronze than the somewhat dull orange-bronze color of Wolverine. Grace also exhibits a small yellow halo around the corolla of ray florets, while Wolverine does not. Grace has a daisy capitulum type, while Wolverine has a spoon-tipped daisy capitulum type. Grace has a more spreading and prolific branching pattern, a smaller diameter of capitulum and an earlier natural season flowering response in New Jersey than Wolverine.

In the following description color references are made to The Royal Horticultural Society Colour Chart. The exact floret color of Grace is not represented in The R.H.S. Colour Chart, and the color values given are those closest to the actual color of Grace. The color values were determined on plant material grown in a controlled greenhouse environment in Salinas, Calif. on Sept. 20, 1989.

Classification:

*Botanical.*—*Dendranthema grandiflora* cv Grace.

*Commercial.*—Flat daisy spray pot mum and garden mum.

INFLORESCENCE

A. Capitulum:

*Form.*—Flat.

*Type.*—Daisy.

*Diameter across face.*—44 to 57 mm when fully opened.

B. Corolla of ray florets:

*Color (general tonality from a distance of three meters).*—Orange-bronze.

*Color (upper surface).*—Base color 13A, heavily overlaid with 169B. Base of ray florets (halo) is 13A.

*Color (under surface).*—Base color 13B, overlaid and streaked with 169B.

*Shape.*—Flat, straight, oblong. Older ray florets convex.

C. Corolla of disc florets:

*Color (mature).*—13A.

*Color (immature).*—Closest to 144B.

D. Reproductive organs:

*Androecium.*—Present on disc florets only; moderate pollen.

*Gynoecium.*—Present on both ray and disc florets.

PLANT

A. General appearance:

*Height.*—Average 28 to 36 cm from soil line at time of flowering, based on June 15 planting in Hightstown, N.J.

*Branching pattern.*—Spreading and prolific.

B. Foliage:

*Color (upper surface).*—147A.

*Color (under surface).*—147B.

*Shape.*—See photograph.

CHART A

COMPARISON OF GRACE AND WOLVERINE

| CHARACTERISTIC | GRACE | WOLVERINE |
|---|---|---|
| Ray floret color | Orange-bronze | Orange-bronze |
| Capitulum form | Flat | Flat |
| Capitulum type | Daisy | Spoon-tipped daisy |
| Branching pattern | Spreading and prolific | Semi-spreading |
| Diameter across face of capitulum | 44 to 57 mm | 63 to 73 mm |
| Controlled response | 7 weeks | 7 weeks |
| Average natural season flower date: | | |
| Salinas, California | August 27 | Not available |
| Hightstown, New Jersey | September 27 | October 2 |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

We claim:

1. A new and distinct Chrysanthemum plant named Grace, as described and illustrated.

* * * * *

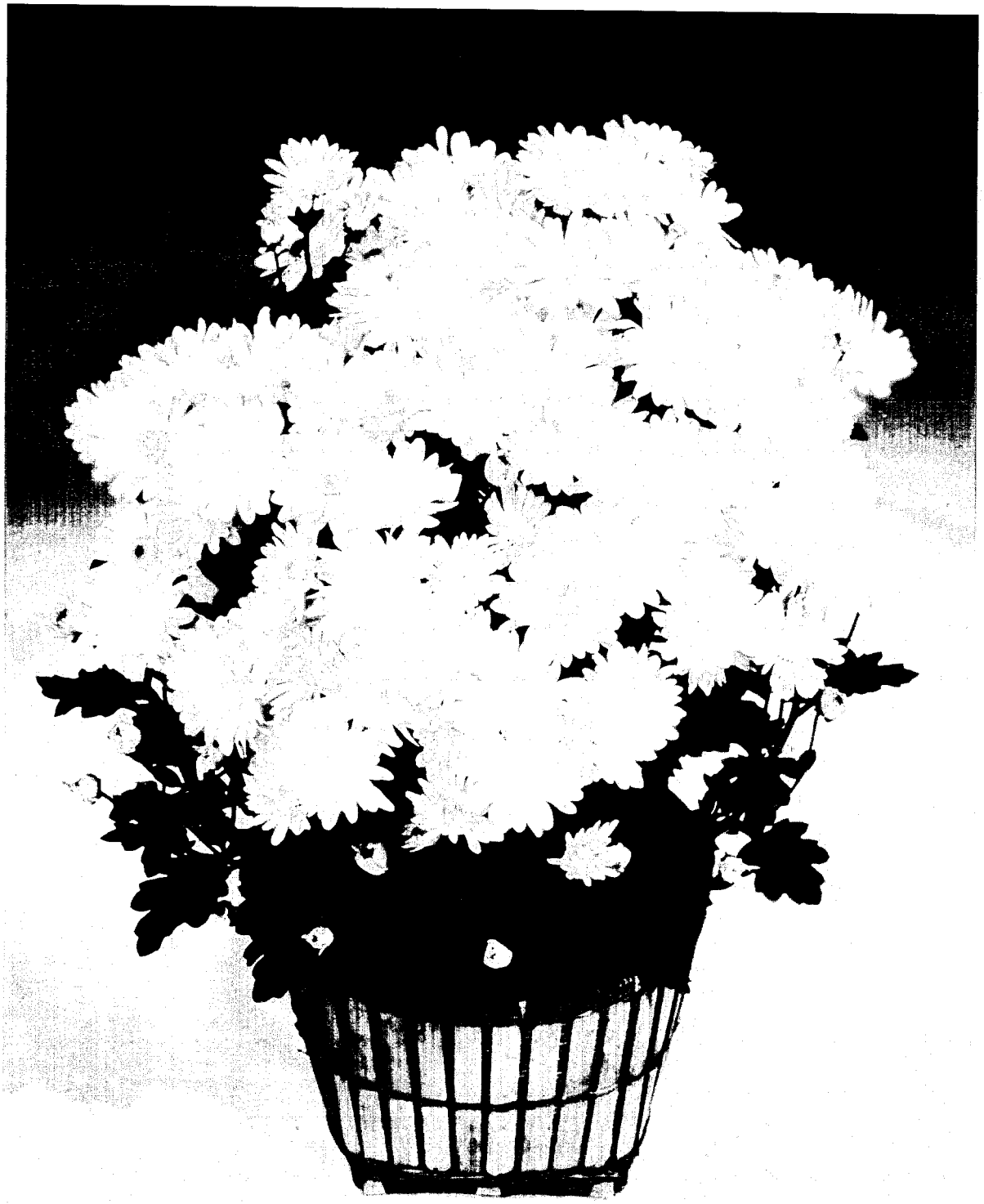

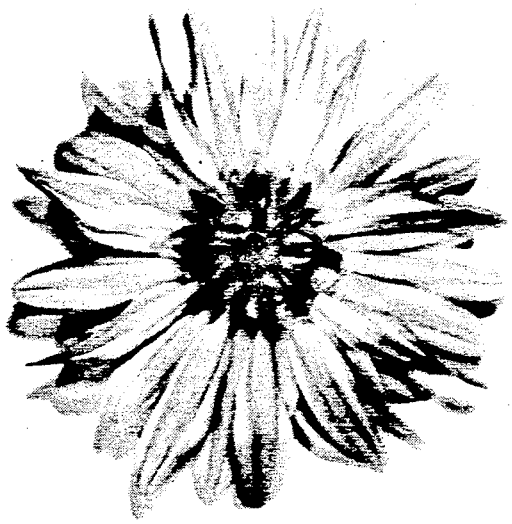
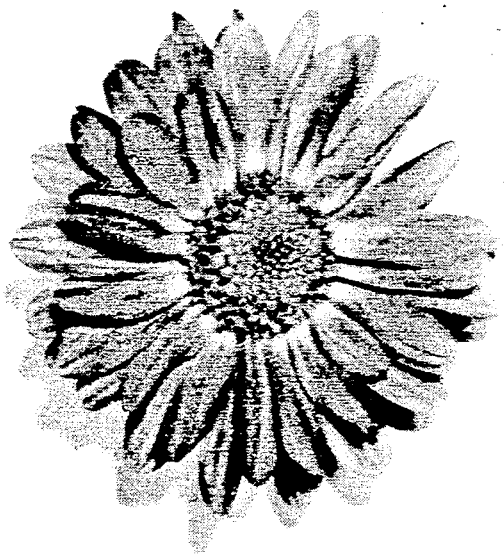
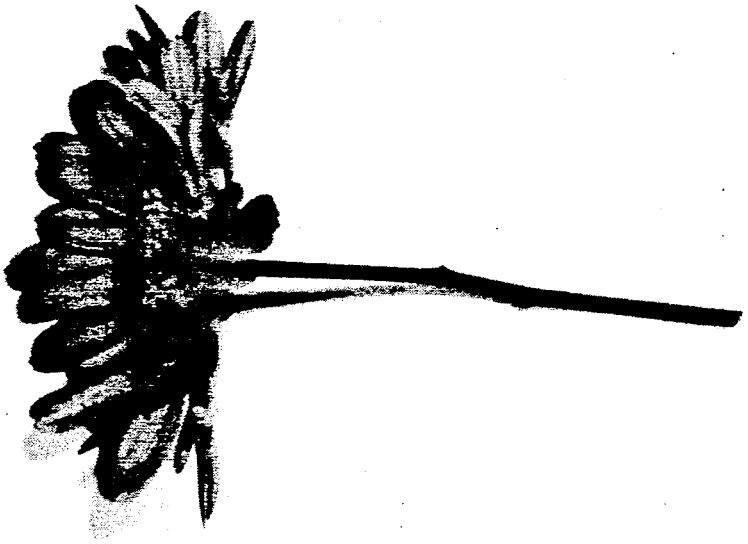

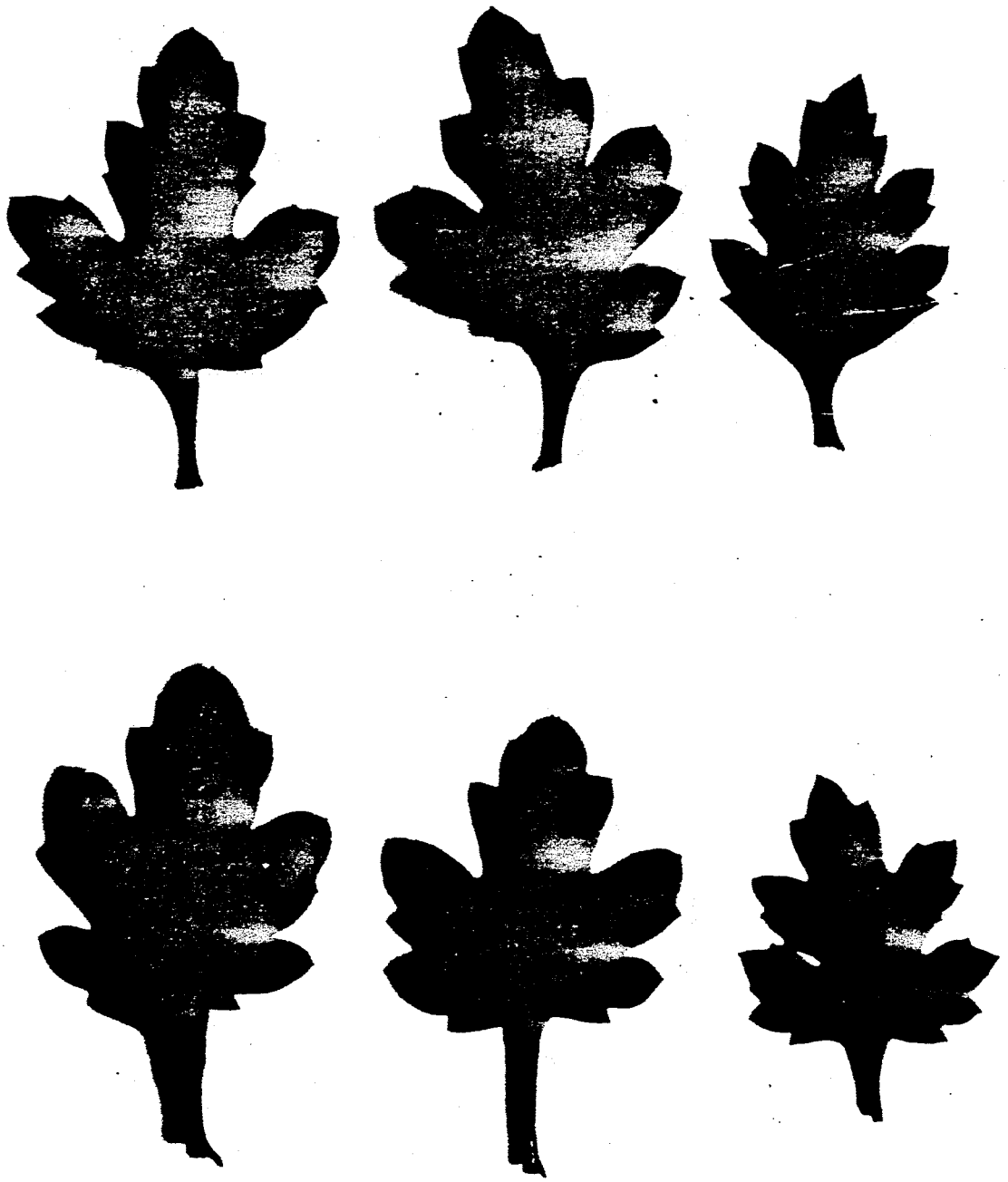

UNITED STATES PATENT AND TRADEMARK OFFICE

CERTIFICATE OF CORRECTION

PATENT NO. : PP 7,642

DATED : September 3, 1991

INVENTOR(S) : MACK et al.

It is certified that error appears in the above-identified patent and that said Letters Patent is hereby corrected as shown below:

Abstract, lines 2, 3, delete "daisy capitulum form; "

Signed and Sealed this

Second Day of November, 1993

Attest:

Bruce Lehman

BRUCE LEHMAN

Attesting Officer

Commissioner of Patents and Trademarks